(12) United States Patent
Liu

(10) Patent No.: US 9,119,570 B2
(45) Date of Patent: Sep. 1, 2015

(54) EYEBALL MOVEMENT MONITORING METHOD AND DEVICE

(75) Inventor: Zhiyong Liu, Beijing (CN)

(73) Assignee: ISEN TECH & TRADING CO., LTD, Beijing (CN)

( * ) Notice: Subject to any disclaimer, the term of this patent is extended or adjusted under 35 U.S.C. 154(b) by 104 days.

(21) Appl. No.: 14/126,676

(22) PCT Filed: Apr. 13, 2012

(86) PCT No.: PCT/CN2012/074011
§ 371 (c)(1),
(2), (4) Date: Dec. 16, 2013

(87) PCT Pub. No.: WO2012/171405
PCT Pub. Date: Dec. 20, 2012

(65) Prior Publication Data
US 2014/0111771 A1   Apr. 24, 2014

(30) Foreign Application Priority Data
Jun. 17, 2011 (CN) .......................... 2011 1 0164766

(51) Int. Cl.
| A61B 3/14 | (2006.01) |
| A61B 3/113 | (2006.01) |
| A61B 3/00 | (2006.01) |
| G06K 9/00 | (2006.01) |
| G06K 9/46 | (2006.01) |
| G06T 7/00 | (2006.01) |

(52) U.S. Cl.
CPC .............. *A61B 3/113* (2013.01); *A61B 3/0025* (2013.01); *G06K 9/00604* (2013.01); *G06K 9/4642* (2013.01); *G06T 7/0012* (2013.01)

(58) Field of Classification Search
CPC ... A61B 3/0025; A61B 3/113; G06K 9/00597
USPC ................. 351/205, 206, 209, 210, 224, 246; 396/51
See application file for complete search history.

(56) References Cited

U.S. PATENT DOCUMENTS 4,973,149 A * 11/1990 Hutchinson ................... 351/210

* cited by examiner

*Primary Examiner* — Mahidere Sahle
(74) *Attorney, Agent, or Firm* — CBM Patent Consulting, LLC

(57) ABSTRACT

An apparatus and method for monitoring the movement of eyeball comprises collecting an image frame of pupil; extracting a pupil pixel set (S); extracting a boundary value of the pupil pixel set; setting a center point based on the boundary value and dividing the pupil pixel set into four quadrant sets (S1, S2, S3 and S4); calculating the coordinate of cross points of the two straight lines and traversing points in the four quadrants, wherein the cross points form a pupil center coordinate set (S5); and calculating an average value of horizontal and vertical directions according to the pupil center coordinate set (S5).

7 Claims, 5 Drawing Sheets

EYEBALL MOVEMENT MONITORING METHOD AND DEVICE

This application is the U.S. national phase of International Application No. PCT/CN2012/074011 Filed 13 Apr. 2012 which designated the U.S. and claims priority to Chinese Application Nos. 201110164766.X filed 17 Jun. 2011, the entire contents of each of which are hereby incorporated by reference.

TECHNICAL FIELD

The invention relates to an eye movement monitoring technique, and more particularly relates to an eye movement monitoring method and an eye movement monitoring device.

BACKGROUND

In the medical field of otoneurology and vestibular function examination, benign positional paroxysmal vertigo (BPPV) pertains to a momentary dizziness induced when the head is moved to a specific position and also a self-limited peripheral vestibular disease. The BPPV has a relatively high incidence which is about 17-20% in all peripheral vertigo. Canalith repositioning procedure of the BPPV is mature and the success is in terms of accurate location on otolith and semicircular canal. Till now, both localization diagnosis and repositioning of the existing BPPV are based on eye movement of the patient through visual inspection of the doctor.

The localization diagnosis and repositioning of the existing BPPV have the following shortages:

1. In many cases, the eye movement is subtle and is neglected by naked eyes easily.
2. Results obtained by observing the eye movement directly by the naked eyes are rough, accompanied with the subjective judgment of the doctor and lacking in quantitative analysis method.
3. Image data of the eye movement of the patient during examination cannot be stored.
4. Without sufficient data during examination, preoperative and postoperative effects cannot be analyzed quantitatively.
5. Due to complex structure, the device cannot be used by the patient conveniently and is not applicable to clinical use.

Above-mentioned shortages in conventional method are easy to affect the localization diagnosis and repositioning of the BPPV. Therefore, a special method and a special device are required urgently to help doctor implement diagnosis and treatment accurately.

SUMMARY OF THE INVENTION

For above problems, the invention provides an eye movement monitoring method, comprising the steps of:

Collecting an image frame of an eye; extracting a pupil pixel set according to the predetermined threshold;

Extracting a boundary value of the pupil pixel set;

Setting a center point based on the boundary value and dividing the pupil pixel set into a first quadrant set, a second quadrant set, a third quadrant set and a fourth quadrant set;

Wherein pixels of the first quadrant set and the third quadrant set form a straight line, and the pixels of the second quadrant set and the fourth quadrant set also form the straight line; calculating the coordinate of crosspoints of the two straight lines and traversing points in the four quadrants, wherein the crosspoints form a pupil center coordinate set; and Calculating an average value of horizontal and vertical directions according to the pupil center coordinate set, wherein the average value is a center point position of the pupil.

The invention further provides an eye movement monitoring device, comprising:

A video image collection device for collecting a video or an image of pupil regularly and converting the video image into an electric signal;

An analysis control device for receiving the electric signal sent from the video image collection device, calculating a position of a pupil based on different gray levels of pixels of the pupil and extracting data of the eye movement at horizontal and vertical directions;

A display device for receiving the original video image as well as the eye movement data analyzed by the analysis control device and displaying the video image and the data of the eye movement at the horizontal and vertical directions in a graphics mode;

A storage device for receiving the image and analysis results sent from the analysis control device, compressing and storing the image and analysis results.

According to the eye movement monitoring method and the eye movement monitoring device, the eye movement image can be observed and recorded directly, and the eye movement state can be analyzed, recorded and displayed in a graphics mode timely.

The real-time image acquisition and analysis technology of the present invention can record and analyze more intuitively and objectively evoked nystagmus in all position of patients, which can accurately confirm diagnosis and evaluate treatment outcome and save the data of eye movement, and also to be conducive to further guide clinical practice and teaching and research work.

FIGURE LEGENDS

SPECIFIC IMPLEMENTATION WAYS

The present invention is described in detail below by with reference to accompanying figures.

Figure 1:
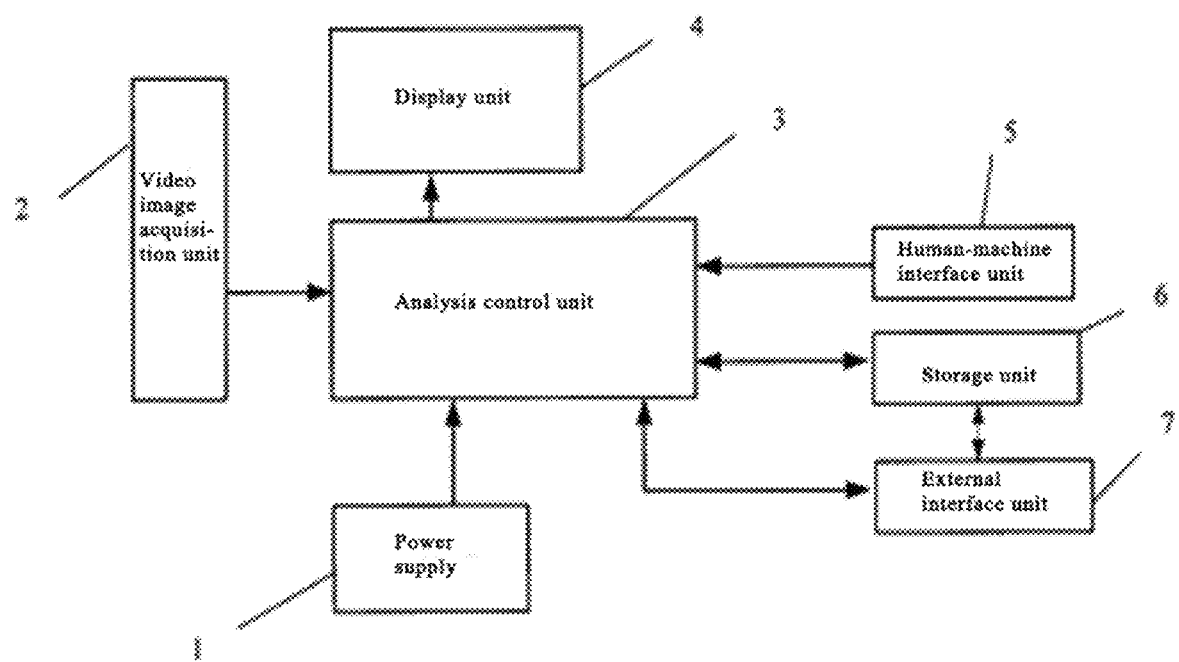
FIG. 1 is a block diagram of eye movement monitoring device of the present invention.

FIG. 1 is a block diagram of eye movement monitoring device of the present invention. The eye movement monitoring device comprising: video image acquisition unit 2, which acquires periodically video or image of the eye, and transfer a video image into an electric signal; analysis control unit 3, which receives the electrical signal send from the video image acquisition unit 2, and subsequently perform an image analysis, extracting the horizontal and vertical motion data of eye movement; display unit 4, which receives the eye movement data analyzed by the analysis control unit 3 and original video images, and displays these video images and presents a graphic display of the horizontal and vertical direction data of eye movement; storage unit 6, which receives the image transmitted from analysis control units 3 and analyzes and stores the results, and also, in order to increase storage efficiency, can compress electric video image signal before storage. And, the mentioned eye movement monitoring device further comprises a power supply unit 1, which may be a battery or mains.

In a further embodiment, the video image acquisition unit 2 includes two sub-acquisition units for collecting a respective eye movement, which can simultaneously acquire the movement of the patient's two eyes, providing richer data for doctor. And, the each sub-acquisition units includes an infrared camera and an infrared light used to fill light for the infrared camera.

In a further implementation, the eye movement monitoring device also includes a human-machine interface unit 5, which is used to the settings of analysis control device for physician, including: setting monitoring device to work in preview mode or video mode, setting the date and time of the instrument, browsing, deleting, and playing the recorded video files, controlling the start, pause and stop of video, and controlling the start, pause, and stop of playing of video files.

In a further embodiment, the eye movement monitoring device also includes an external interface unit 7, which is connected to the storage unit 6, and can export the data stored in the storage unit 6 to the outside through the interface unit. For example, these exported data can be used to other studies by higher performance computers.

Figure 2:
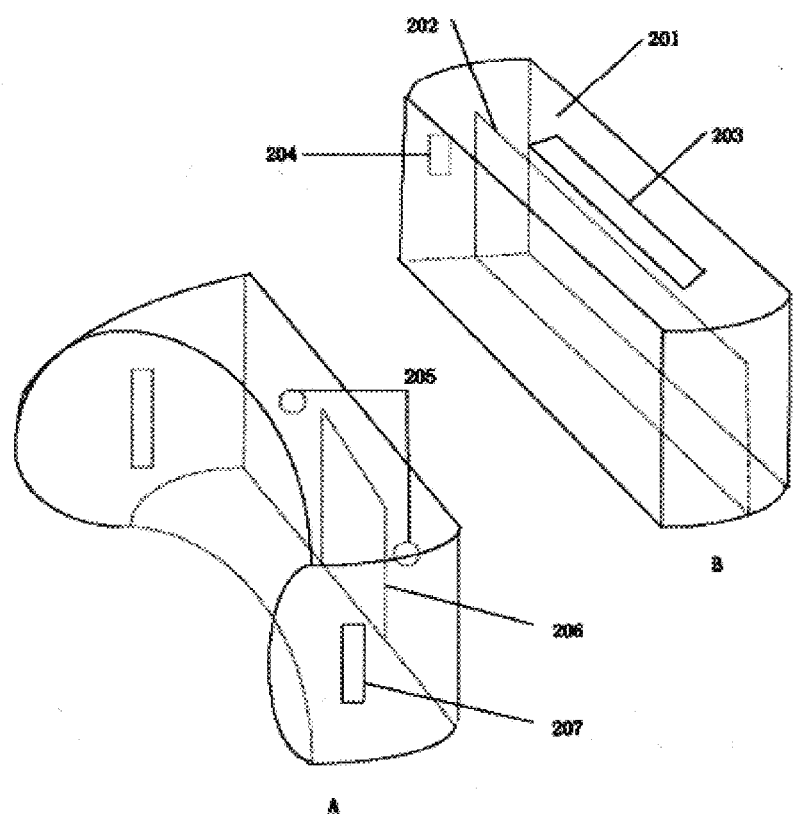
FIG. 2 is an exploded perspective view of an implementation of the eye movement monitoring device of the present invention.
Figure 3:
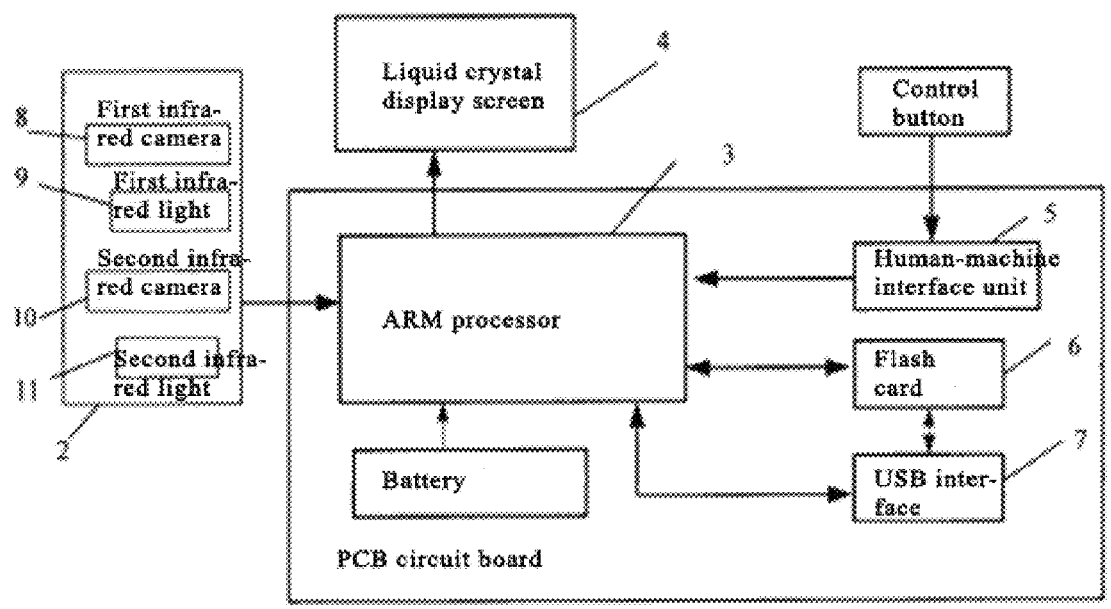
FIG. 3 is an electrical functional block diagram of eye movement monitoring device as shown in FIG. 2.

FIG. 2 is an exploded perspective view of an implementation of the eye movement monitoring device of the present invention. FIG. 3 is an electrical functional block diagram of eye movement monitoring device. As shown in FIG. 2, Part A (wearing part) and Part B (analysis-display part) can be snapped together, and, of course, also can be connected using other connection means, such as adhesive and screw. The housing of Part A and Part B is made of plastic to reduce the weight of the device. Part A has a curved contour line fitting a human face, so that keeping the eye can be closed as close as possible to Part A.

Both sides of Part A has a headband buckle 207 for linking headband, and when performing an inspection procedure, the inspection device is fixed to the head of the user by the headband, making the eye align to the camera 205. In this embodiment, the camera uses a pinhole infrared camera, and video image acquisition unit 2 includes a first infrared camera 8 and a first infrared light 9, and a second infrared camera 10 and a second infrared light 11. Also, in this embodiment, the supply of power is provided by a battery, and the battery is located in the battery compartment 206, so that making the device can be more portable. The wear side of Part A also has been added a rubber gasket to increase the wear-comfort.

The interior of Part B has a circuit board PCB 202. The PCB board 202 integrated an analysis control unit 3, a human-machine interface unit 5, a storage unit 6, and an external interface unit 7. The analysis control unit 3 can be ARM processor, MCU, or others with computing function. The storage unit 6 can be a Flash card, EEPROM, or other non-volatile memory. The external interface unit 7 can be a USB interface, or others. The side of Part B has the opening of USB interface 204.

The liquid crystal display screen 201 also use other display units, such as LCD, which is connected to the analysis control unit 3 in PCB circuit board. The upper portion of Part B has control button 203, through which the doctor can send an electrical control signal to human-machine interface unit 5.

Figure 4:
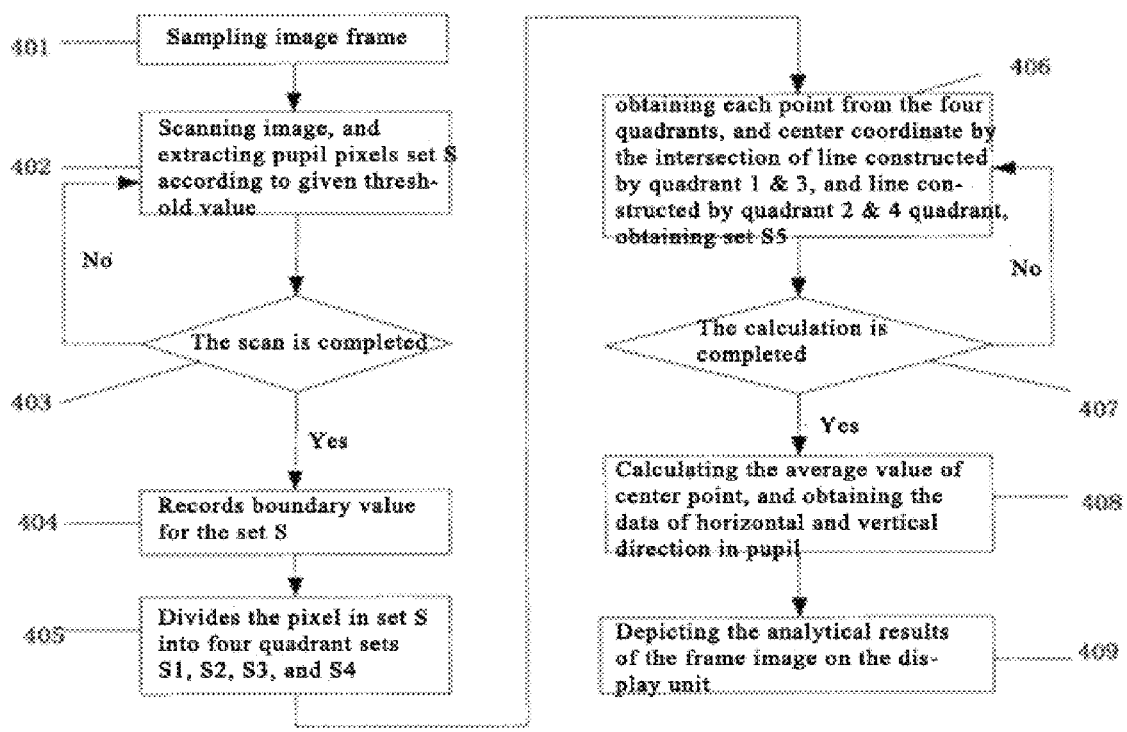
FIG. 4 is a flowchart of eye movement monitoring method of the present invention.

Next, the implemented eye movement monitoring method using the eye movement monitoring device of the present invention is described with reference to the flowchart of FIG. 4.

In step 401, a frame image is sampled from the video image acquisition unit 2, and the sampling interval of each frame image can be set, e.g. 33 ms. Analysis control unit 3 and video image acquisition unit 2 are in real-time connection/transmission status, which can directly extract images captured by the camera.

In step 402, analysis control unit 3, which scans all pixels of the image from top to bottom and from left to right, can assume the lower left corner of the image as coordinates (0,0), and, according to a predetermined threshold gray-level, determine initially whether the pixel belongs to the pupil pixels. The threshold is preferably set at 35, and, when the gray-level of scanned pixel is less than 35, it is considered that the pixel belongs to the pupil pixel, and the pixel is added to the pupil pixel set S;

In step 403, to determine whether the image scanning is completed, if the scanning is not completed, then continue scanning, and if completed, go to step 404;

In step 404, to remove noise point presenting possibly in the set S and to correct the boundary of the set in the step. For example, for any point in the set S, if the four neighboring points in left, right, upper and lower are all not point in set S, the point can be determined as a noise point, and the point will be removed from set S. If the point has impact on boundary value, then reset the boundary value.

In step 405, according to the boundary value recorded in step 404, a central point is set, and according to the central point, set S is divided into four quadrants (quadrant 1, 2, 3, and 4), thereby obtaining four quadrant sets S1, S2, S3, and S4;

In step 406, each pixel from the four quadrants is obtained, with which the pixels of 1 quadrant and 3 quadrant construct a straight line, and the pixels of 2 quadrant and 4 quadrant construct a straight line. Subsequently the coordinates of the intersection of two straight lines are calculated and the points in the four quadrants are traversed, and then the obtained intersection is put into the pupil center coordinate set S5;

In step 407, to determine whether the calculation is completed, if not completed, then continue, and if completed, then go to step 408;

In step 408, according to the set S5, the average values of horizontal and vertical direction are calculated, and then the value is the center point coordinate of the pupil;

In step 409, the analytical results of the frame image are depicted on the LCD screen. If performing continuous acquisition, the flow returns to step 401 to start processing the next frame.

According to the sampling frequency and total number of image frames, the x values of the drawing coordinate system and the coordinates (origin of the coordinate system is at the lower left corner of image) are calculated; according to the data of horizontal and vertical direction of current image are calculated the y coordinate value; and then drawing.

Figure 5:
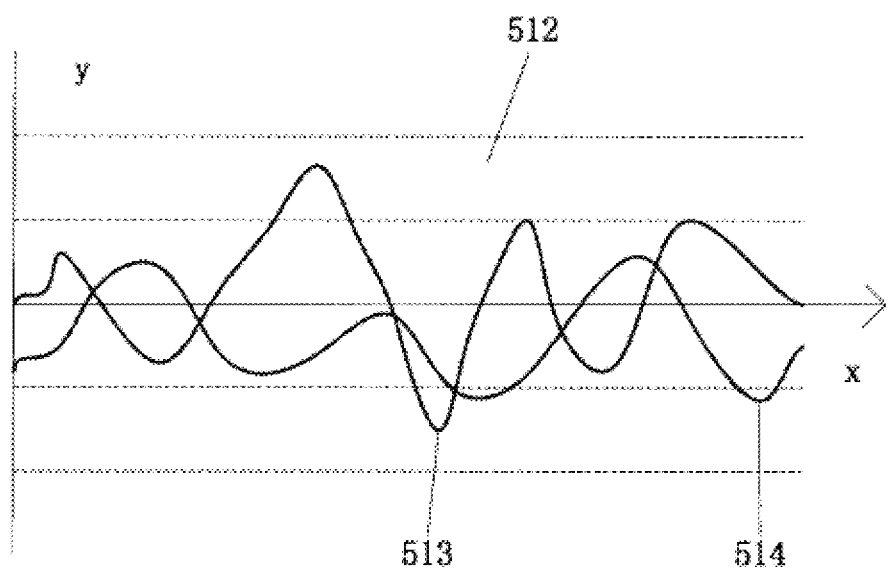
FIG. 5 is a schematic diagram of eye movement monitoring results of the present invention.

FIG. 5 shows a schematic diagram of eye movement monitoring results. In the data of the horizontal and vertical direction displayed in the coordinate system 512, the curve 513 represents the data in horizontal direction, and the curve 514 represents the data in the vertical direction, and when the values of the curve of horizontal data are gradually increasing at Y axis, which means that pupil is moving rightward, whereas when the values are gradually decreasing, which means that pupil is moving leftward; when the values of the curve of vertical data are gradually increasing at Y axis, which means that pupil is moving upward, whereas when the values are gradually decreasing, which means that pupil is moving downward; whereby, doctor obtains clearly the movement trajectory of the eye from two curves.

The above described embodiment is the preferred one of the present invention. It should be noted that for skilled persons in the field, based on the same principles of the invention, the embodiment that also can be made several other variations and modifications and the application of the technical solution in the other similar fields, all are fell within the protective scope of the present invention.

What is claimed is:

1. A method for monitoring the movement of eyeball, comprises the following steps: collecting an image frame of pupil; extracting a pupil pixel set (S) according to a predetermined threshold; extracting a boundary value of the pupil pixel set; setting a center point based on the boundary value and dividing the pupil pixel set into a first quadrant set (S1), a second quadrant set (S2), a third quadrant set (S3) and a fourth quadrant set (S4), wherein pixels of the first quadrant set (S1) and the third quadrant set (S3) form a straight line, and the pixels of the second quadrant set (S2) and the fourth quadrant set (S4) also form a straight line; calculating the coordinate of crosspoints of the two straight lines and traversing points in the four quadrants, wherein the crosspoints form a pupil center coordinate set (S5); and calculating an average value of horizontal and vertical directions according to the pupil center coordinate set (S5), wherein the average value is a center point position of the pupil.

2. The method for monitoring the movement of eyeball according to claim 1, characterized in that the method further comprises the step of removing any point from the pupil pixel set (S) if left, right, upper and lower adjacent points of the point are not within the set.

3. The method for monitoring the movement of eyeball according to claim 2, characterized in that the method further comprises the step of resetting the boundary value if the point affects the boundary value.

4. The method for monitoring the movement of eyeball according to claim 1, characterized in that the image frame is collected by an infrared camera device.

5. The method for monitoring the movement of eyeball according to claim 1, characterized in that the threshold is the gray threshold equal to 35.

6. An apparatus for monitoring the movement of eyeball, characterized in that the apparatus comprises: a video image collection device for collecting a video or an image of an eye regularly and converting the video image into an electric signal; an analysis control device for receiving the electric signal sent from the video image collection device, calculating a position of a pupil based on different gray levels of pixels of the pupil and extracting data of the eye movement at horizontal and vertical directions; a display device for receiving the original video image as well as the eye movement data analyzed by the analysis control device and displaying the video image and the data of the eye movement at the horizontal and vertical directions in a graphics mode; a storage device for receiving the image and analysis results sent from the analysis control device, compressing and storing the image and analysis results: wherein the analysis control device is configured for extracting a pupil pixel set (S) from the image sent by the video image collection device according to a predetermined threshold; extracting a boundary value of the pupil pixel set; setting a center point based on the boundary value and divide the pupil pixel set into a first quadrant set (S1), a second quadrant set (S2), a third quadrant set (S3) and a fourth quadrant set (S4), wherein pixels of the first quadrant set (S1) and the third quadrant set (S3) form a straight line, and the pixels of the second quadrant set (S2) and the fourth quadrant set (S4) also form the straight line; calculate the coordinate of crosspoints of the two straight lines and traverse points in the four quadrants, wherein the crosspoints form a pupil center coordinate set (S5); and calculating an average value of horizontal and vertical directions according to the pupil center coordinate set (S5), wherein the average value is a center point position of the pupil.

7. The apparatus for monitoring the movement of eyeball according to claim 6, characterized in that the apparatus for monitoring the movement of eyeball further comprises an external interface device connected with an external computing device.

* * * * *